United States Patent [19]

Granz

[11] Patent Number: 5,072,722
[45] Date of Patent: Dec. 17, 1991

[54] DEVICE FOR THE SPATIAL ULTRASONIC LOCATION OF CALCULI

[75] Inventor: Bernd Granz, Oberasbach, Fed. Rep. of Germany

[73] Assignee: Siemens Aktiengesellschaft, Berlin & Munich, Fed. Rep. of Germany

[21] Appl. No.: 598,810

[22] Filed: Oct. 17, 1990

Related U.S. Application Data

[63] Continuation of Ser. No. 350,716, May 11, 1989, abandoned.

[30] Foreign Application Priority Data

May 25, 1988 [DE] Fed. Rep. of Germany ....... 3817726

[51] Int. Cl.⁵ .............................................. A61B 17/22
[52] U.S. Cl. ............................ 128/24 EL; 128/660.03
[58] Field of Search ....................... 128/24 EL, 660.03; 606/127, 128

[56] References Cited

U.S. PATENT DOCUMENTS

| | | | |
|---|---|---|---|
| 4,157,665 | 6/1979 | Bridoux et al. | 128/661.01 |
| 4,526,168 | 7/1985 | Hassler et al. | 128/303 R |
| 4,610,249 | 9/1986 | Mokofski et al. | 128/24 A |
| 4,617,931 | 10/1986 | Dory | 128/24 A |
| 4,742,494 | 5/1988 | Breimesser et al. | 367/358 |
| 4,757,820 | 7/1988 | Itoh | 128/660.03 |
| 4,771,787 | 9/1988 | Wurster et al. | 128/24 A |
| 4,787,394 | 11/1988 | Ogura | 128/660.03 |
| 4,803,995 | 2/1989 | Ishida et al. | 606/128 |
| 4,834,106 | 5/1989 | Hassler et al. | 128/660.03 |

FOREIGN PATENT DOCUMENTS

| | | | |
|---|---|---|---|
| 3743883 | 7/1988 | Fed. Rep. of Germany ... | 128/24 EL |
| 3703333 | 8/1988 | Fed. Rep. of Germany ...... | 128/328 |
| 3703336 | 8/1988 | Fed. Rep. of Germany ...... | 128/328 |
| 3703338 | 8/1988 | Fed. Rep. of Germany ...... | 128/328 |

OTHER PUBLICATIONS

Acoustical Holography, vol. 5, 1973, "A New, High-Performance Ultrasonic Camera", Philip S. Green et al.
Acoustical Image, vol. 15, 1987, "A Two Dimensional PVDF Transducer Matrix as a Receiver in an Ultrasonic Transmission Camera", Granz et al.

Primary Examiner—Francis Jaworski
Assistant Examiner—Scott R. Akers
Attorney, Agent, or Firm—Kenyon & Kenyon

[57] ABSTRACT

The invention relates to a device for the spatial, ultrasonic location of concrements found in the body of a living being, which are to be located at the focus of an ultrasonic shock wave so as to be destroyed in a lithotritor. According to the invention, an ultrasonic camera, which works in the reflection mode, is provided for the ultrasonic location procedure focal region which is adjusted to an object plane, which contains the focus of the ultrasonic shock wave. In this way, information from sectional planes of the body can be made available to the user, making it easier to position the concrement securely in the focus of the ultrasonic shock wave.

18 Claims, 2 Drawing Sheets

DEVICE FOR THE SPATIAL ULTRASONIC LOCATION OF CALCULI

This application is a continuation of application Ser. No. 350,716, filed 5/11/89 now abandoned.

BACKGROUND OF THE INVENTION

1. Field of the Invention

The invention relates to a device for the spatial ultrasonic location of concrements.

2. Related Art

So-called lithotriptors are used to remove concrements, for example kidney stones or gallstones, found in the body of a living thing. With these lithotriptors, such concrements can be destroyed, without being touched, by means of focused ultrasonic shock waves. By applying ultrasonic shock waves, surgery or the introduction of probes into the body of a patient can be avoided. Thus, the danger of infection associated with such interventions is also avoided.

To prevent damaging healthy tissue in the area surrounding the concrement, the concrement to be destroyed must be positioned as exactly as possible in the focus of the shock wave. X-rays or ultrasonics, for example, can be used to locate the concrement spatially, as is required for the exact positioning.

An important advantage in an ultrasonic location of the concrement to be destroyed is that, simultaneously with the location procedure, information can be gained concerning the conditions for the sound propagation of the shock wave. This information is obtained when the area in the body of the living thing, which is irradiated by the ultrasonic shock wave, is also covered by the ultrasonic waves used for the location procedure.

For example, devices for the spatial ultrasonic location of concrements are known from German Patent No. 27 22 252. They receive the reflections and measure the propagation delay of pulses, which are emitted by an ultrasonic transmitter and reflect off the concrement or scatter, to locate the concrement. In one specific embodiment, an ultrasonic transmitter and an ultrasonic receiver are mounted in the wall of a coupling device. Their axes of rotation intersect at an angle of 30° in the focus of the ultrasonic shock wave. This coupling device contains the shock wave source and can be placed externally on a patient. Instead of using a separate ultrasonic transmitter, an arrangement is also provided, whereby the shock-wave source, operated with reduced intensity, is itself used as an ultrasonic transmitter to locate the concrement. By means of pressure sensors, which are arranged in the wall of the coupling device, the scattered shocks emanating from the concrement are received. The position of the concrement is then determined from these differences in propagation delay. In a further specific embodiment, a swivelling ultrasonic transformer is provided. In accordance with the B-scan process, it generates a sectional view in a plane containing the focus of the ultrasonic shock wave.

As far as a reliable and simple positioning of the concrement in the focus of the ultrasonic shock wave is concerned, of the known ultrasonic detection devices, the device working according to the B-scan process is more advantageous than devices working according to the A-scan process. This is due to the fact that, on the one hand, the two-dimensional B-scan gives a clear impression of the geometric proportions of the area surrounding the concrement and, on the other hand, one can interpret it more reliably than a one-dimensional A-scan.

However, echographic B-scan processes have the disadvantage that only sectional planes of a body can be depicted, which run perpendicular to the axis of the body and thus, for the most part, parallel to the direction of propagation of the ultrasonic waves. Thus, the image information, which is available to the user for positioning the focus or the concrement, is of an unfamiliar object plane, which is ill-suited for sharp focusing. In the case of the known device, for example, when a concrement is displaced lateral to the image plane in the image relative to the focus, this corresponds to a defocusing. This displacement of the concerement can consist of a lateral, as well as of an axial displacement, relative to the direction of propagation of the ultrasonic shock wave.

A further disadvantage of the know device in this respect is also that, in particular, the lateral resolution of an echographic sectional view, which is conditional on the width of the sound cone used for scanning, is unsatisfactory and hinders an exact axial location and positioning of the concrement in the focus of the ultrasonic shock wave.

An ultrasonic imaging system for diagnostic purposes, which operates in accordance with the principle of an optical episcope, is known from "Acoustical Holography", vol. 5, Plenum Publ. Corp., New York 1973, Ed. P. S. Green, pages 493 to 503. This system, called an ultrasonic camera, allows sectional views of the patient to be displayed, which run perpendicularly to the sagittal sectional planes of the ultrasonic echography. For this purpose, the patient to be examined is "illuminated" with ultrasound. Either the transmitted or reflected ultrasonic waves, scattered by the patient, are focused by means of a lens system onto an image plane and converted into electric signals by a linear receiving array arranged there. With the help of two contra-rotating prisms arranged in the path of rays, the image generated by the lens system is deflected sinusoidally, so that a two-dimensional image can be constructed with the receiving signal measured on the linear receiving array. The image frequency attained in this way amounts to approximately 15 Hz, so that one can already speak of a real-time image presentation. A higher image frequency, however, is not possible. This is due to the fact, that the higher rotational frequency of the prisms, which this would require, would cause turbulence in the sound-carrying liquid and thus lead to interference in the sound propagation and a reduction of the image quality. The depth level of the sectional plane focused by the ultrasonic camera results, according to the principles of geometric optics, from the characteristics of representation of the acoustical imaging system being used, the image distance of the receiving array, and the position of the body relative to the then established focal area in the object field.

An ultrasonic transmission camera, which enables a higher image frequency without mechanical moving parts with a simplified design of the scanning device, is revealed, for example, in "Acoustical Imaging", vol 15, Plenum Publ. Corp., New York 1987, Ed. H. W. Jones, pages 213 to 225. Therein, instead of a linear receiving array, a two-dimensional receiver matrix consisting of 29×128 transducer elements is provided. The electric signals impinging on the individual transducer elements are read out one after another and merged into a two-dimensional image, whose image frequency amounts to approximately 25 Hz. The area of the receiver matrix which is sensitive to ultrasound is formed, thereby, of a thin PVDF foil, which is pressed against a matrix-shaped electrode arrangement. A further development of this type of receiver matrix is known, for example, from the U.S. Pat. No. 4,742,494.

SUMMARY OF THE INVENTION

The object of the present invention is to provide a device for the ultrasonic location of concrements situated in the body of a living thing, which will enable a simple and exact positioning of the concrement in the focus of an ultrasonic shock wave.

The mentioned objective is solved, according to the invention, by a device for the spatial, ultrasonic location of concrements found in the body of a living thing, which are to be located at the focus of an ultrasonic shock wave of a lithotriptor so as to be destroyed, wherein the improvement comprises an ultrasonic camera, which works in the reflection mode, provided for the ultrasonic location procedure, the camera having a focal region that is adjusted to an object plane which contains, at least approximately, the focus of the ultrasonic shock wave.

When an ultrasonic locating device is used, which functions according to the principle of an ultrasonic camera working in reflection mode, the user is provided with a locator device, which generates a real-time image of a sectional plane of the body lying outside of the sagittal plane and which facilitates exact positioning. In particular, a sectional plane of the body can be selected which runs parallel to the focal plane of the ultrasonic shock wave. The user consequently has image information available from an object plane which is especially suited for the sharp focusing of the lithotriptor. The image-forming conditions of the ultrasonic camera are adjusted thereby, so that an area of the object field that contains the focus of the ultrasonic shock wave is sharply focused. The focus is thereby permanently allocated to a predetermined image area on a monitor, for example the center of the image. To the observer, the concrement to be destroyed appears sharp and in the center of the image, only if it actually lies in the focus of the ultrasonic shock wave. Every time an actual axial maladjustment occurs outside of the area of the depth of focus, it can be recognized as an insufficient focus on the monitor image. Conditional on the image-forming principle used in the ultrasonic camera, the resolution is the same in each lateral direction within the sectional plane. Since, in addition, with an ultrasonic camera, a stereoscopic real-time image with a high lateral resolution can be generated for the observer, positioning the concrement exactly in the focus of the ultrasonic shock wave is made considerably easier.

Further possible advantageous refinements of the invention include:
a) the ultrasonic camera contains an ultrasonic receiver which comprises a plurality of transducer elements arranged in the shape of a matrix;
b) the center axis of the ultrasonic shock wave coincides, at least approximately, with the imaging axis, situated in the object field, of the ultrasonic camera;
c) an acoustical beam-splitter is arranged in the path of rays of the ultrasonic shock wave;
d) a pivoting beam-splitter is provided;
d) a common ultrasonic transmitter is provided to generate ultrasonic waves for the ultrasonic location procedure and to generate the ultrasonic shock wave;
e) the acoustical beam-splitter is arranged between a planar ultrasonic transmitter and a lens for focusing the ultrasonic shock wave;
f) an ultrasonic transmitter is provided for the ultrasonic location procedure and said transmitter is surrounded by a shock wave transmitter and is arranged in a central area of the shock wave transmitter; and
g) a common ultrasonic transmitter with several transducer elements is provided, said transducer elements being controllable independently from each other.

BRIEF DESCRIPTION OF THE DRAWINGS

For further clarification of the invention, reference is made to the drawings, in which.

DETAILED DESCRIPTION OF THE PREFERRED EMBODIMENTS

Figure 1:
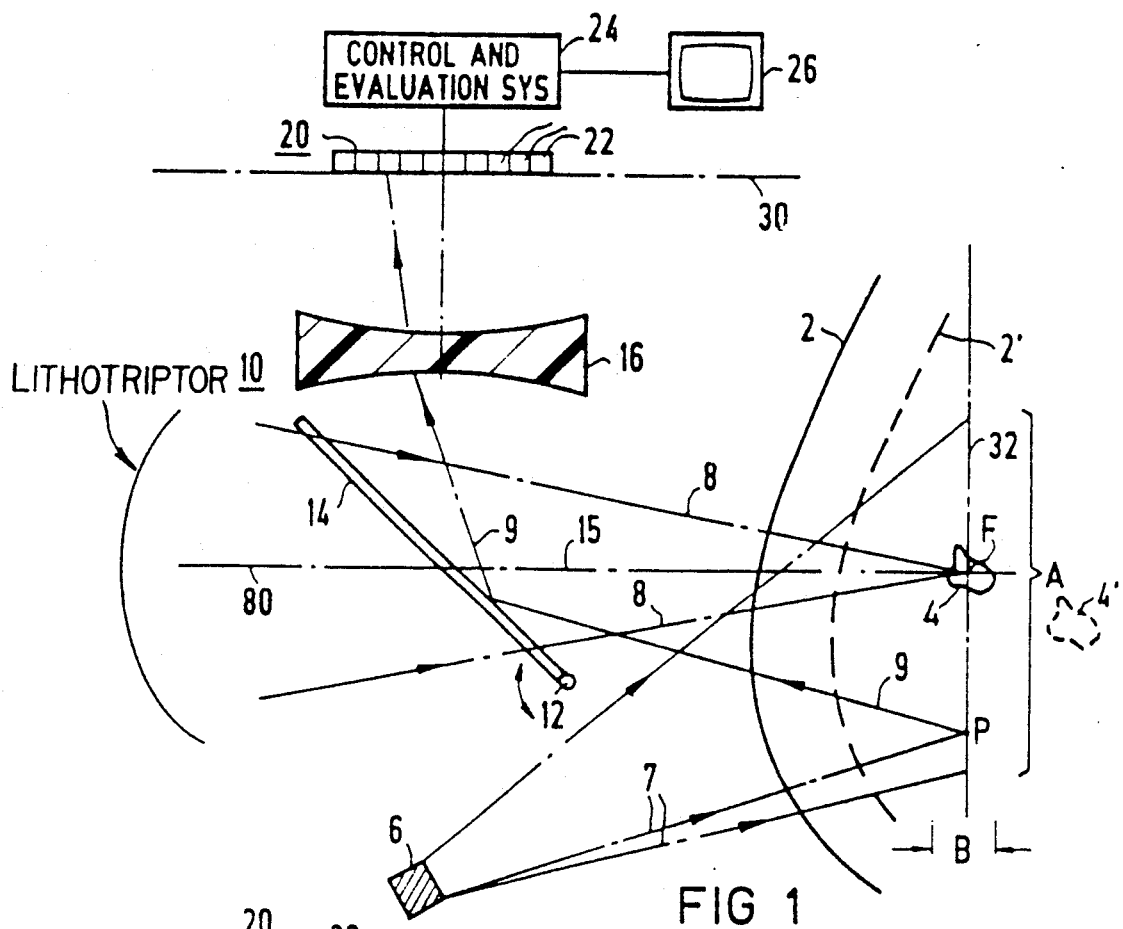
FIG. 1 illustrates the device for ultrasonic location, according to the invention and FIGS. 2, 3 and 4 schematically depict further advantageous refinements of the invention.

According to FIG. 1, a concrement 4 is located in the body 2 of a living thing and is to be destroyed with the help of an ultrasonic shock wave 8. This ultrasonic shock wave 8 is generated by a focused shock wave transmitter of a lithotriptor, not shown. The concrement 4 is detected with an ultrasonic camera working in reflection mode, which contains an ultrasonic transmitter 6 for the continuous or pulsed acoustic irradiation with ultrasonic waves 7 of a spatial area of the body 2 containing the focus F of the ultrasonic shock wave 8. The ultrasonic camera also contains an imaging system 10, as well as an ultrasonic receiver 20, which is arranged in an image plane 30 of the imaging system 10. The ultrasonic receiver 20 contains a plurality of transducer elements 22 and, for purposes of signal analysis, it is connected to a control and evaluation system 24 which outputs the ultrasound pressure distribution received by the ultrasonic receiver 20 into an image onto the screen of a monitor 26. In an advantageous refinement of the invention, the ultrasonic receiver 20 contains a plurality of transducer elements 22, which are arranged in the form of a matrix. An especially suitable transformer arrangement is known, for example, from U.S. Pat. No. 4,742,494. The shock wave transmitter and the ultrasonic camera are situated, for example, in a coupling device, not shown in the FIG., which is filled with a sound-carrying liquid and is set up over an elastic rubber bellows on the surface of the body 2. In a preferred refinement of the invention, an aperture closed with a PVDF-foil is provided in the wall of the coupling device at the location of the ultrasonic transmitter 20. An electrode matrix, analogous to the known device from the German Published Patent Application 36 28 705, is pressed on this aperture from the outside.

In the example of FIG. 1, the imaging system 10 comprises an acoustical beam-splitter 14, for example a planar, thin plate of polystyrene PS and an acoustical lens 16, preferably of polystyrene PB as well, which focuses the ultrasonic waves 9 reflected by the body 2 on to the receiving surface of the ultrasonic receiver 20. The beam-splitter 14 is preferably arranged at a 45° angle on the center axis 80 of the ultrasonic shock wave 8 in the path of rays of the ultrasonic shock wave 8, so that the path of rays inside the ultrasonic camera is interlaced with the path of rays of the ultrasonic shock wave 8, at least in the body 2. As a result of this interlacing, structures can also be detected in the course of ultrasonic location, which lie between the surface of the body 2 and the focus F of the ultrasonic shock wave 8 and which could have a disturbing effect on the propagation of the ultrasonic shock waves 8. The beam-splitter 14 is arranged, thereby, at least during the location procedure, in the path of rays of the ultrasonic shock wave 8. In a preferred specific embodiment, the beam-splitter is removed from the path of rays, when the concrement 4 is bombarded with the ultrasonic shock wave 8. According to the example of FIG. 1, a beam-splitter 14, which can pivot around an axis of rotation 12, is forseen for this purpose. In the case of an ultrasonic transmitter 6 arranged, according to FIG. 1, outside of the path of rays of the ultrasonic shock wave 8, an acoustical opaque mirror can be used for the location procedure, in place of a beam-splitter 14. For example, a metal plate can be pivoted or inserted in the path of rays of the ultrasonic shock wave 8.

The focal length of the acoustical lens 16 and the image distance of the ultrasonic receiver 20 are selected so that the focal region or area B of the ultrasonic camera is adjusted to an object plane 32 which contains the focus F of the ultrasonic shock wave 8. Conditional on the final lateral resolution of the ultrasonic receiver 20, which amounts to about 2 mm in all lateral directions, and depending on the sound wavelength, which is now considerable relative to the geometric dimensions of the imaging system 10, not only an object plane 32 will be sharply focused, as would result analogously to the principles of geometric optics, but a focal area B would be in sharp focus, as well. Its depth amounts to approximately 10 mm to 20 mm, depending on the wavelength of the ultrasonic waves 7 transmitted by the ultrasonic transmitter 6. Within this focal area B, the surroundings of each point P, which is situated on the object plane 32 and from which emanates a scattered or reflected ultrasonic wave 9, are therefore sharply focused on the ultrasonic receiver 20.

In the preferred specific embodiment according to FIG. 1, the center axis 80 of the ultrasonic shock wave 8 coincides with the imaging axis 15 of the imaging system 10, which runs in the object field between the body and the beam-splitter, so that the object plane 32 is situated perpendicularly on the center axis 80. The sectional view of the body 2 displayed on the monitor 26 corresponds then to a sectional plane of the body, which runs perpendicularly to the direction of propagation of the ultrasonic shock wave 8, so that each actual lateral maladjustment of the concrement 4 in the focal plane corresponds to a lateral displacement, given by the imaging scale of the imaging system 10, of the still sharply focused concrement on the screen of the monitor 26. The positioning of a concrement 4', situated outside of the focus F, can be accomplished using the usual focus control method in optics For example, a sharp image of the concrement 4' is initially generated on the monitor 26 by a relative axial displacement of the body 2' and of the ultrasonic camera, which is rigidly connected to the lithotriptor. Then, with lateral displacements, which appear directly on the monitor as lateral displacements, as well, the concrement is guided into the focus zone of the ultrasonic shock wave 8, which corresponds for example, to the designated center of image of the monitor 26. In addition, the arrangement according to FIG. 1 guarantees that the ultrasonic wave 9 emanating from the object plane 32 crosses the same spatial area in the body 2 as does the ultrasonic shock wave 8.

Figure 2:
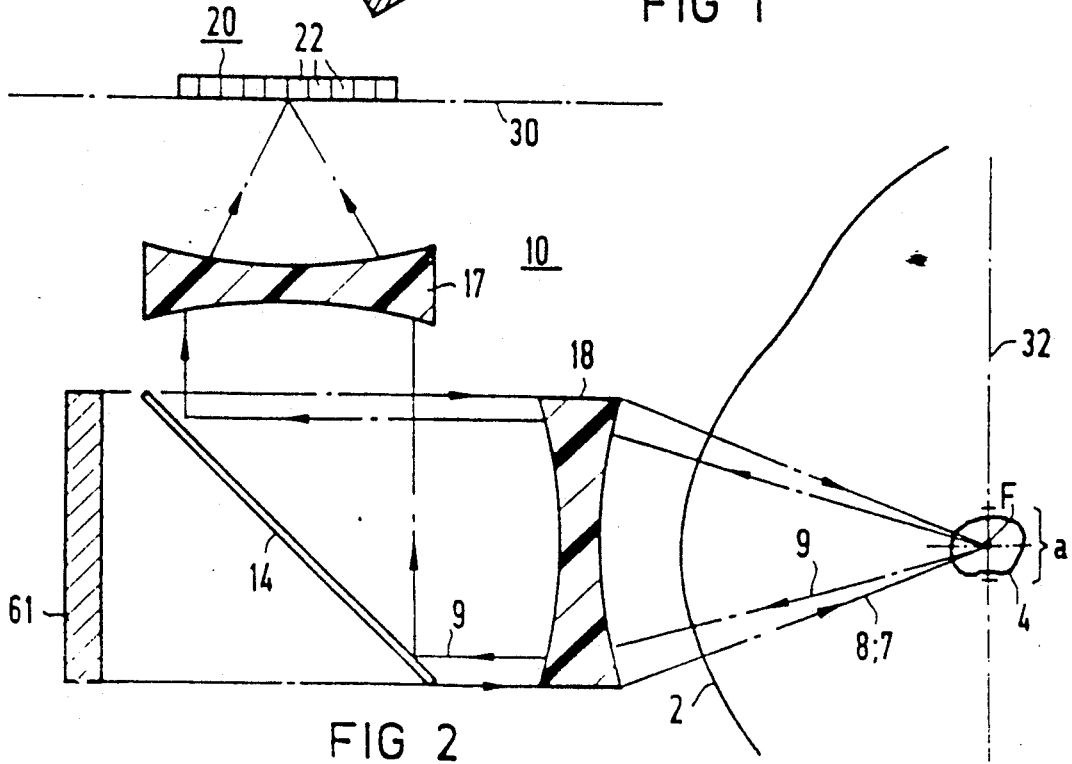

A specific embodiment is provided according to FIG. 2, whereby the ultrasonic camera has an ultrasonic transmitter used for ultrasonic location which is also used as a shock transmitter to generate the ultrasonic shock wave 8. This common ultrasonic transmitter 61 may be a piezoelectric transmitter 61, for example. During the location procedure, this ultrasonic transmitter 61 generates ultrasonic waves 7 in c.w. (continuous wave) operation, whose intensity is reduced relative to the intensity of the ultrasonic shock wave 8. In this arrangement, contrary to the arrangement of FIG. 1, only a small area of the object plane 32 assigned to the image plane 30 is illuminated, even during the location procedure. However, its lateral extent a is adequate, even in the area near the focus, to focus the concrement 4 sharply in the center of image of the ultrasonic receiver 20. The fact that the focal position of the ultrasonic wave 7 can be axially displaced relative to the focal position of the ultrasonic shock wave 8 is not significant in this case, since the adjusted focal area of the ultrasonic camera is independent of the focus of the ultrasonic wave 7.

In the case of a planar ultrasonic transmitter 61, the acoustical beam-splitter 14 is preferably arranged, during the ultrasonic location procedure, between the ultrasonic transmitter 61 and a lens 18, which serves to focus the ultrasonic shock wave 8, so that this lens 18, together with a lens 17, make up part of the imaging system 10 of the ultrasonic camera. The advantage of this arrangement is that it allows the position of the focus F of the ultrasonic shock wave 8 to be monitored at the same time. During the operation of the lithotriptor, it can happen, for example, as a result of the mechanical loads produced by the ultrasonic shock waves, that the ultrasonic transmitter 61 or the lens 18 are displaced in their mounting supports. Such a maladjustment can cause the focused spot of the ultrasonic shock wave 8 to be situated outside of the original focus. However, since the ultrasonic transmitter 61 and the lens 18 are parts of the ultrasonic camera, during the ultrasonic location procedure, the illuminated spatial area is no longer focused symmetrically around the middle point of the receiving surface of the ultrasonic receiver 20. Thus, already during the ultrasonic location procedure, the observer can determine that the focus of the lithotriptor is out of alignment and, if necessary, resort to measures to correct the focal position.

Figure 3:
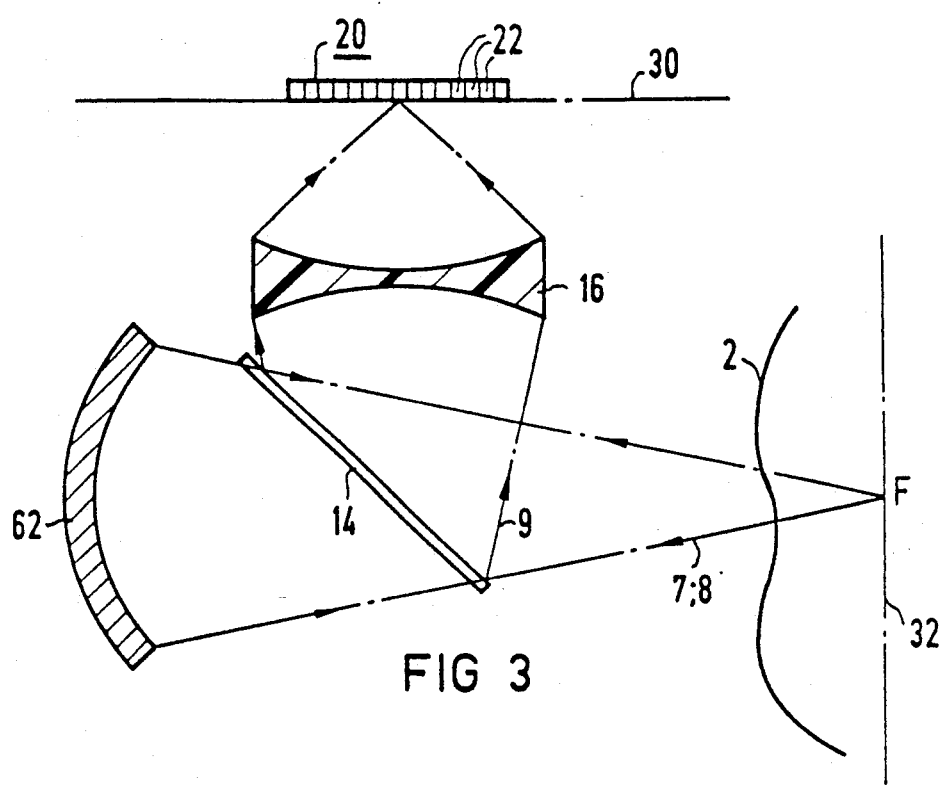

This is also possible in an arrangement according to FIG. 3, whereby the focused ultrasonic shock wave 8 is generated by means of a spherical ultrasonic transmitter 62, so that a lens is no longer needed to focus the ultrasonic shock wave 8.

Figure 4:
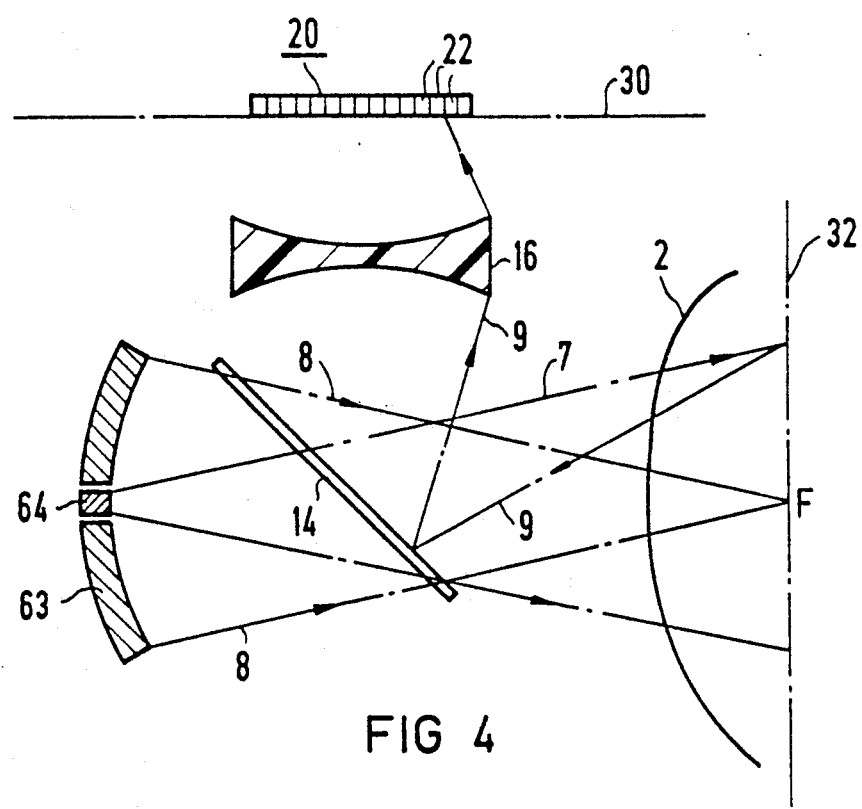

An ultrasonic transmitter 64 is provided for the ultrasonic camera in the arrangement according to FIG. 4. It is surrounded by a shock wave transmitter 63 and is arranged in the central area of this transmitter 63. In the example of FIG. 4, the ultrasonic transmitter 64 is mounted in a central bore of a spherical shock wave transmitter 63. The advantage of this arrangement, as in the specific embodiment of FIG. 1, is that to collect the ultrasonic image, a large area of the object field is illuminated and, in this connection, a larger sectional plane of the body 2 is focused on the monitor, so that the search for the concrement is facilitated. Also, as a result of this arrangement, a nearly complete overlapping of the area irradiated by the ultrasonic wave 7 with the area irradiated by the ultrasonic shock wave 8 is achieved, and structures which could interfere with the propagation of the ultrasonic shock wave 8 are detected with greater certainty.

Annular or matrix-shaped transducer arrays are also suited as a common ultrasonic transmitter for the lithotriptor and the ultrasonic camera, as revealed for example in the U.S. Pat. No. 4,526,168, whereby the individual transducer elements of the transducer arrays or the focusing of the ultrasonic shock wave are controlled separately from each other and with phase lag. It is then sufficient in the ultrasonic location procedure, if only a few of the transducer elements, (for example, only one single central transducer element) are used to irradiate the body 2.

I claim:

1. In combination with a lithotriptor having a shock wave transmitter to generate an ultrasonic shock wave focused at a focus point, a device for the spatial location of concrements found in the body of a living thing, comprising:

an ultrasonic camera securely connected to the lithotriptor including: an ultrasonic transmitter generating an ultrasonic wave to be reflected by a volume part of the body; an acoustical beam-splitter arranged in the path of the ultrasonic shock wave and reflecting the ultrasonic wave reflected by said volume part of the body; an acoustical lens focusing the ultrasonic wave reflected by said volume part of the body; an ultrasonic receiver disposed in an image plane and having a plurality of transducer elements arranged in a matrix receiving the ultrasonic wave reflected by the volume part of the body, said camera working in a reflection mode, said camera having an object plane containing the focus point of the ultrasonic shock wave and forming the image of the object plane on the image plane, whereby the concrements can be located at the focus point of the ultrasonic shock wave emanating form the lithotriptor so that the concrements can be destroyed.

2. The combination of claim 1 wherein the ultrasonic shock wave has a center axis and said ultrasonic camera has an imaging axis, the center axis and said imaging axis being approximately coincident between the shock wave transmitter and the object plane.

3. The combination of claim 2 wherein said ultrasonic camera comprises said ultrasonic transmitter used in locating the concrements, said ultrasonic transmitter being surrounded by said shock wave transmitter of said lithotriptor, and said ultrasonic transmitter being arranged in a central area of the shock wave transmitter.

4. The combination of claim 2 wherein said beam-splitter is supported to pivot around an axis of rotation.

5. A method for locating concrements found in a body of a living thing at the focus of an ultrasonic shock wave emanating from a lithotriptor so that the concrements can be destroyed, the method comprising the steps of:

a. securely coupling an ultrasonic camera to the lithotriptor having a focus point of the ultrasonic shock wave;

b. forming an image with the ultrasonic camera having an object plane containing the focus point of the ultrasonic shock wave;

c. operating the ultrasonic camera in a reflection mode for locating the concrements in the body;

d. shifting the living thing or the ultrasonic camera until the concrement is located at the focus of the ultrasonic shock wave.

6. The method of claim 5 wherein the step of securely coupling comprises the step of arranging an imaging axis of the ultrasonic camera and a center axis of the ultrasonic shock wave so that the imaging axis and the center axis are approximately coincident between the shock wave transmitter and the object plane.

7. The method of claim 5 further comprising the step of arranging an acoustical beam-splitter in the path of rays of the ultrasonic shock wave.

8. The method of claim 7 further comprising the step of pivoting the acoustical beam-splitter around an axis of rotation.

9. The method of claim 7 wherein the step of securely coupling the ultrasonic camera to the lithotriptor comprises the step of disposing an ultrasonic transmitter in a central area of a shock wave transmitter of the lithotriptor.

10. The method of claim 7 further comprising the step of generating an ultrasonic wave and the ultrasonic shock wave from a common ultrasonic transmitter having a plurality of transducer elements.

11. The method of claim 10 wherein each of the transducer elements generate ultrasonic waves and ultrasonic shock waves independently of the other transducer elements.

12. The method of claim 10 wherein the common ultrasonic transmitter is planar.

13. The method of claim 10 further comprising the step of focusing the ultrasonic shock wave with a lens.

14. In combination with a lithotriptor, a device for the spatial location of concrements found in the body of a living thing, comprising:

an ultrasonic transmitter generating an ultrasonic shock wave focused at a focus point and an ultrasonic wave to be reflected by a volume part of the body; and an ultrasonic camera securely connected to the lithotriptor, wherein said ultrasonic transmitter is common to the lithotriptor and said camera and said camera includes: an acoustical beam-splitter arranged in the path of the ultrasonic shock wave and reflecting the ultrasonic wave reflected by the body; an acoustical lens focusing the ultrasonic wave reflected by the volume part of the body; an ultrasonic receiver disposed in an image plane and having a plurality of transducer elements arranged in a matrix receiving the ultrasonic wave reflected by the volume part of the body, said camera working in a reflection mode, said camera having an object plane containing the focus point of the ultrasonic shock wave and forming the image of the object plane on the image plane, the ultrasonic shock wave having a center axis and said ultrasonic camera having an imaging axis, the center axis and said imaging axis being approximately coincident between the shock wave transmitter and the object plane, whereby the concrements can be located at the focus point of the ultrasonic shock wave emanating from the lithotriptor so that the concrements can be destroyed.

15. In combination with a lithotriptor having a shock wave transmitter to generate an ultrasonic shock wave focused at a focus point, a device for the spatial location of concrements found in the body of a living thing, comprising, an ultrasonic camera securely connected to the lithotriptor including: an ultrasonic transmitter generating an ultrasonic wave to be reflected by a volume part of the body; an acoustical beam-splitter arranged in the path of the ultrasonic shock wave and reflecting the ultrasonic wave reflected by the volume part of the body; an acoustical lens focusing the ultrasonic wave reflected by the volume part of the body; an ultrasonic receiver disposed in an image plane and having a plurality of transducer elements arranged in a matrix receiving the ultrasonic wave reflected by the volume part of the body, said camera working in a reflection mode, said camera having an object plane substantially perpendicular to the propagation direction of the ultrasonic wave between the object plane and the beam splitter to form an image on the image plane, whereby the concrements can be located at the focus point of the ultrasonic shock wave emanating from the lithotriptor so that the concrements can be destroyed.

16. The combination of claim 14 wherein said common ultrasonic transmitter comprises a plurality of transducer elements, each of said transducer elements being able to generate the ultrasonic waves and the ultrasonic shock waves independently of the other transducer elements.

17. The combination of claim 15 wherein said common ultrasonic transmitter is planar.

18. The combination of claim 17 further comprising a lens disposed in the path of the ultrasonic shock wave, said acoustical beam-splitter being arranged between said planar ultrasonic transmitter and said lens.

* * * * *